United States Patent [19]

Satoh et al.

[11] Patent Number: 5,840,928
[45] Date of Patent: Nov. 24, 1998

US005840928A

[54] METHOD FOR PRODUCTION OF 3-FORMYL-TETRAHYDROFURAN

[75] Inventors: Kenichi Satoh; Toshio Kitashima; Yutaka Chiba; Katsutoshi Kinoshita; Kenji Kodaka, all of Chiba, Japan

[73] Assignee: Mitsui Chemicals, Inc., Tokyo, Japan

[21] Appl. No.: 813,348

[22] Filed: Mar. 7, 1997

[30] Foreign Application Priority Data

Mar. 12, 1996 [JP] Japan ................................. 8-054878

[51] Int. Cl.$^6$ ............................................. C07D 307/12
[52] U.S. Cl. .................................................... 549/483
[58] Field of Search ..................................... 549/483

[56] References Cited

U.S. PATENT DOCUMENTS 4,376,208  3/1983  Vietti ...................................... 549/475

FOREIGN PATENT DOCUMENTS 0054986   6/1982   European Pat. Off. .
0627399   12/1994  European Pat. Off. .
082956833 11/1996  Japan .

OTHER PUBLICATIONS

Chemical Abstracts, vol. 122, No. 15, Apr. 10, 1995, Columbus, Ohio, Abstract No. 187564, XP002030721, abstract; RN 13468–92–3 JP 06340652.

Chemical Abstracts, vol. vol. 120, No. 13, Mar. 29, 1994, Columbus, Ohio, Abstract No. 163335, XP002030722, abstract and NEFTEKHIMIYA, vol. 33, No. 2, 1993, pp. 102–113, XP000197389, E.V. Slivinsky et al.

Weinheimer et al, "Rearrangement of Diphenan to 9, 10–dihydro–9–Phenanthrol by Potassium Amide and Dehydration to Phenanthrene. Results with 1,8–Naphthalan, Phthalan, and 2,5–Dihydrofuran", *Journal of Organic Chemistry*, vol. 18, pp. 801–805 (1953).

Barry et al, "Tripheylphosphine–Tetrachloromethane Promoted Chlorination and Cyclodehydratin of Simple Diols", *Journal of Organic Chemistry*, vol. 46, pp. 3361–3364 (1981).

Polo et al, "Regioselective Hydroformulation of Cyclic Vinyl and Allyl Ethers with Rhodium Catalysts. Crucial Influence of the Size of the Phosphorus Cocatalyst", *Organometallics*, vol. 11, pp. 3525–3533 (1992).

Poloet al, "Low–Pressure Selective Hydroformylation of 2,3– and 2,5–Dihydrofuran with a Rhydium Catalyst. Unexpected Influence of the Auxillary Ligand Tris(o–t–burylphenyl)Phosphite", *J. Chem. Soc., Chem. Commun.*, pp. 600–601 (1990).

Fernandez et al, "Synthesis of Acetals from Alkenes by One–Pot Hydroformylation–Transacetalization Reactions Catalysed by Rhodium Complexes and Pyridnium p–Toluenesulphonate", *Tetrahedron Letters*, vol. 35, No. 15, pp. 2361–2364 (1994).

*Primary Examiner*—Jane Fan
*Attorney, Agent, or Firm*—Burns, Doane, Swecker & Mathis, L.L.P.

[57] ABSTRACT

3-Formyltetrahydrofuran is prepared by reacting 2,5-dihydrofuran with hydrogen and carbon monoxide in the presence of a group VIII metal compound and tris(2-t-butyl-5-methylphenyl) phosphite.

2 Claims, No Drawings

METHOD FOR PRODUCTION OF 3-FORMYL-TETRAHYDROFURAN

BACKGROUND OF THE INVENTION

1. Field of the Invention

This invention relates to a process for the hydroformylation of 2,5-dihydrofuran by using a group VIII metal compound as catalyst. The 3-formyltetrahydrofuran prepared by this process is useful as an intermediate for the synthesis of drugs and agricultural chemicals.

2. Description of the Related Art

The reaction for forming an aldehyde by reacting an olefin with carbon monoxide and hydrogen in the presence of a group VIII metal compound is known as the hydroformylation reaction. Among group VIII metal compounds, rhodium compounds are known to be excellent in reactivity and selectivity. However, since rhodium carbonyl is unstable, rhodium is used in a form modified with a ligand. As this ligand, there may generally be used phosphorus compounds such as trialkylphosphines, triarylphosphines and triaryl phosphites (EP Publication No. 627,399), arsenic compounds and antimony compounds.

2,5-Dihydrofuran can readily be obtained by preparing 2-butyne-1,4-diol from acetylene by the Reppe synthesis, hydrogenating it partially to form cis-2-butene-1,4-diol, and then effecting its ring closing with the aid of an acid or the like [see, for example, J. Org. Chem., Vol. 18, pp. 801–805 (1953) and J. Org. Chem., Vol. 46, pp. 3361–3364 (1981)].

Processes for formylating 2,5-dihydrofuran at the 3-position are disclosed, for example, in a report of J. C. Bayon et al. [Organometallics, Vol. 11(11), pp. 3525–3533 (1992); J.C.S. Chem. commun., 600–601 (1990)], a report of Fernandez et al. [Tetrahedron letters, Vol. 15, p. 2361–2364 (1994)], and U.S. Pat. No. 4,376,208.

In the report of Bayon et al. [Organometallics, Vol. 11(11), pp. 3525–3533 (1992); J.C.S. Chem. commun., 600–601 (1990)], the ratio of the substrate to the catalyst is as low as 400:1. In view of the fact that rhodium used as catalyst is very expensive, this process is very disadvantageous from an industrial point of view. Moreover, the reaction tends to stop halfway. Although the reaction proceeded with a high degree of conversion in a single example where tris(o-t-butylphenyl) phosphite was added, the selectivity for the 3-position was low. The ratio of the substrate to the catalyst is also low in U.S. Pat. No. 4,376,208. Although the selectivity ratio between the 2and 3-positions is reported to be 5:95 in the Examples thereof, examination by the present inventors, in which the ratio of the substrate to the catalyst was set higher, has revealed that 3-formyltetrahydrofuran cannot be obtained with the described high selectivity under the conditions of the Examples.

In order to obtain 3-formyltetrahydrofuran efficiently, it is desirable to keep the reaction temperature low. However, in the processes described in these references, the reaction rate tends to be significantly reduced at low temperatures. In order to avoid this problem and achieve an industrially satisfactory reaction rate, it is conceivable to use a rhodium catalyst in large amounts. However, rhodium catalysts are very expensive.

EP Publication No. 54,986 discloses a process for the hydroformylation of olefins with the aid of a rhodium catalyst modified with a certain phosphite. This process has the advantage that even olefins difficult to subject to hydroformylation can be hydroformylated at high reaction rates and only a small amount of a catalyst is required. However, even where such a phosphite is used, satisfactory results cannot be obtained from the viewpoint of selectivity for the 3-position. Moreover, this process has a serious problem in that, when the hydroformylation reaction of 2,5-dihydrofuran is carried out with the reaction temperature kept low, the reaction rate is high in its initial stage, but the reaction stops at a low degree of conversion.

SUMMARY OF THE INVENTION

It is an object of the present invention to provide a process for preparing 3-formyltetrahydrofuran efficiently by hydroformylating 2,5-dihydrofuran at an economically and industrially satisfactory reaction rate and selectivity while using a small amount of rhodium.

The present inventors made intensive investigations with a view to accomplishing the above-described object and have now discovered that, when tris(2-t-butyl-5-methylphenyl) phosphite is used as a ligand, 2,5-dihydrofuran can be hydroformylated at the 3-position by use of a small amount of a hydroformylation catalyst, with good selectivity for the 3-position, with high efficiency, and at a satisfactory reaction rate. The present invention has been completed on the basis of this discovery.

Thus, the present invention relates to a process for the preparation of 3-formyltetrahydrofuran which comprises reacting 2,5-dihydrofuran with hydrogen and carbon monoxide in the presence of a group VIII metal compound and tris(2-t-butyl-5-methylphenyl) phosphite.

In the hydroformylation reaction of 2,5-dihydrofuran, the present invention permits the 3-position of 2,5-dihydrofuran to be selectively and efficiently hydroformylated at a high reaction rate. The amount of catalyst used for this purpose may be very small. Accordingly, the present invention provides an industrially useful process for the preparation of 3-formyltetrahydrofuran. In particular, the process of the present invention is characterized by the use of tris(2-t-butyl-5-methylphenyl) phosphite. Thus, 3-formyltetrahydrofuran can be obtained in high yields according to a process which is much more advantageous from an industrial point of view than conventional processes.

DETAILED DESCRIPTION OF THE INVENTION AND PREFERRED EMBODIMENTS

The group VIII metal compound used as catalyst in the hydroformylation of the present invention may be selected from compounds of rhodium, cobalt and iridium. Among others, rhodium compounds are preferred. Specific examples thereof include $Rh_4(CO)_{12}$, $Rh_6(CO)_{16}$, $Rh(acetylacetonato)(CO)_2$, $RhH(CO)(PPh_3)_3$, $Rh(acetylacetonato)(CO)(PPh_3)$, rhodium oxide, rhodium chloride, rhodium acetylacetate and rhodium acetate. The molar ratio of the catalyst to 2,5-dihydrofuran is generally in the range of 1:100 to 1:500,000 and preferably 1:1,000 to 1:100,000.

The molar ratio of the group VIII metal compound used as catalyst to tris(2-t-butyl-5-methylphenyl) phosphite is in the range of 1:1 to 1:1,000, preferably 1:10 to 1:500, and more preferably 1:20 to 1:100.

In the present invention, tris(2-t-butyl-5-methylphenyl) phosphite is exclusively used as a ligand for the catalyst, and it is utterly unknown whether other ligands exhibit an equal effect or not. Examination by the present inventors have revealed that the desired effect is not achieved by using other phosphites, suggesting that the effect of the present invention is peculiar to tris (2-t-butyl-5-methylphenyl) phosphite.

In the hydroformylation of the present invention, 2,5-dihydrofuran is preferably used as the starting material and solvent. However, the reaction may be carried out in the presence of an inert solvent for the purpose of recovering the catalyst. Inert solvents useful for this purpose include methanol, ethanol, propanol, dichloromethane, trichloromethane, dichloroethane, benzene, toluene, xylene, dimethylformamide, N-methylpyrrolidone, N,N-dimethylimidazolidinone, diglyme and the like.

The reaction temperature is suitably in the range of 20° to 150° C. and preferably 50° to 60° C.

The reaction pressure may range from 0 to 150 atmospheres. Pressures above this limit are disadvantageous, for example, because the size of the reactor is increased. It is preferable to use a pressure in the range of 10 to 80 atmospheres.

The volume ratio of hydrogen to carbon monoxide in the gaseous mixture thereof is preferably in the range of 1/5 to 10/1 and more preferably 1/2 to 2/1.

After completion of the reaction, 3-formyltetrahydrofuran is distilled from the reaction mixture and then purified by fractional distillation as desired.

Now, the subject matter of the present invention is more specifically explained with reference to the following example and reference examples.

EXAMPLE 1

A 200 ml autoclave made of stainless steel was charged with 9.2 mg of trans-[RhH(CO)(PPh$_3$)$_3$], 208.3 mg of tris (2-t-butyl-5-methylphenyl) phosphite and 17.2 g of 2,5-dihydrofuran. Then, the autoclave was charged with a gaseous mixture composed of carbon monoxide and hydrogen in a volume ratio of 1:1 until a pressure of 80 atmospheres was reached, and heated to 55° C. over a period of 30 minutes.

After the autoclave was held at 55° C. for 7 hours and then allowed to cool, the reaction product was analyzed by gas chromatography. The degree of conversion of the starting material was 97% and the selectivity for 3-formyltetrahydrofuran was 93%.

The turnover of the catalyst was 24,500, indicating that the reaction proceeds by use of a very small amount of the catalyst.

REFERENCE EXAMPLE 1

A 200 ml autoclave made of stainless steel was charged with 9.2 mg of trans-[RhH(CO)(PPh$_3$)$_3$], 208.3 mg of tris (2-phenylphenyl) phosphite and 17.2 g of 2,5-dihydrofuran. Then, the autoclave was charged with a gaseous mixture composed of carbon monoxide and hydrogen in a volume ratio of 1:1 until a pressure of 80 atmospheres was reached, and heated to 55° C. over a period of 30 minutes.

After the autoclave was held at 55° C. for 6 hours and then allowed to cool, the reaction product was analyzed by gas chromatography. The degree of conversion of the starting material was 99% and the selectivity for 3-formyltetrahydrofuran was 83%.

REFERENCE EXAMPLE 2

A 200 ml autoclave made of stainless steel was charged with 9.2 mg of trans-[RhH(CO)(PPh$_3$)$_3$], 208.3 mg of tris (2-t-butyl-4-methylphenyl) phosphite and 17.2 g of 2,5-dihydrofuran. Then, the autoclave was charged with a gaseous mixture composed of carbon monoxide and hydrogen in a volume ratio of 1:1 until a pressure of 80 atmospheres was reached, and heated to 55° C. over a period of 30 minutes.

After the autoclave was held at 55° C. for 7 hours and then allowed to cool, the reaction product was analyzed by gas chromatography. The degree of conversion of the starting material was 98% and the selectivity for 3-formyltetrahydrofuran was 81%.

REFERENCE EXAMPLE 3

A 200 ml autoclave made of stainless steel was charged with 9.2 mg of trans-[RhH(CO)(PPh$_3$)$_3$], 208.3 mg of tris (2-t-butyl-5-methylphenyl) phosphite and 17.2 g of 2,5-dihydrofuran. Then, the autoclave was charged with a gaseous mixture composed of carbon monoxide and hydrogen in a volume ratio of 1:1 until a pressure of 80 atmospheres was reached, and heated to 75° C. over a period of 30 minutes.

After the autoclave was held at 75° C. for 7 hours and then allowed to cool, the reaction product was analyzed by gas chromatography. The degree of conversion of the starting material was 98% and the selectivity for 3-formyltetrahydrofuran was 59%.

What is claimed is:

1. A process for the preparation of 3-formyltetrahydrofuran which consists essentially of reacting 2,5-dihydrofuran with hydrogen and carbon monoxide in the range of 50° to 60° C. in the presence of a group VIII metal compound and tris(2-t-butyl-5-methylphenyl) phosphite to form 3-formyltetrahydrofuran.

2. The process of claim 1 wherein the group VIII metal compound is a rhodium compound.

* * * * *